United States Patent [19]
Etheredge, III

[11] Patent Number: 5,201,733
[45] Date of Patent: Apr. 13, 1993

[54] METHOD AND APPARATUS FOR INTERNAL FIXATION OF FRACTURES

[76] Inventor: James L. Etheredge, III, 935 Thora Blvd., Shreveport, La. 71106

[21] Appl. No.: 823,253

[22] Filed: Jan. 21, 1992

[51] Int. Cl.$^5$ .............................................. A61F 5/04
[52] U.S. Cl. ............................................ 606/53; 606/60
[58] Field of Search .................... 606/53, 60, 62, 64, 606/69, 72, 73

[56] References Cited

U.S. PATENT DOCUMENTS

| | | | |
|---|---|---|---|
| 2,242,003 | 5/1941 | Lorenzo | 128/92 |
| 3,030,951 | 4/1962 | Mandarino | 128/92 |
| 3,463,148 | 8/1969 | Treace | 606/69 |
| 3,528,085 | 9/1970 | Reynolds, Jr. | 606/69 |
| 3,579,831 | 5/1971 | Stevens | 32/10 |
| 3,739,773 | 6/1973 | Schmitt et al. | 606/62 |
| 3,741,205 | 6/1973 | Markolf et al. | 606/69 X |
| 4,059,102 | 11/1977 | Devas | 128/92 |
| 4,338,926 | 6/1982 | Kummer et al. | 606/62 X |
| 4,457,301 | 7/1984 | Walker | 606/62 |
| 4,524,765 | 6/1985 | Dezbikowski | 606/69 |
| 4,539,981 | 9/1985 | Tunc | 128/92 |
| 4,711,234 | 12/1987 | Vives et al. | 128/92 |
| 4,776,329 | 10/1988 | Treharne | 128/92 |
| 4,858,603 | 8/1989 | Clemow et al. | 128/92 |
| 4,973,333 | 11/1990 | Treharne | 606/77 |
| 5,062,843 | 11/1991 | Mahoney III | 606/53 |
| 5,129,901 | 7/1992 | Decoste | 606/62 X |

Primary Examiner—Robert A. Hafer
Assistant Examiner—Sam Rimell
Attorney, Agent, or Firm—John M. Harrison

[57] ABSTRACT

A method and apparatus for internal fixation of fractures, which method includes the steps of initially aligning the fractured bone and bone segments, drilling pilot holes in the bone and bone segments to receive non-metallic screws and/or pins, inserting the non-metallic screws and/or pins in the drilled pilot holes to temporarily maintain alignment of the bone and bone fragments, applying one or more metal reconstruction plates to the bone and bone fragments, drilling additional pilot holes in the bone and bone fragments to receive metal screws and/or pins and inserting the metal screws and/or pins through the holes in the metal reconstruction plate into the pilot holes in the bone and bone fragments without regard to the location of the non-metallic pins and/or screws, to permanently fix the bone fragments and bone in correct anatomical configuration.

11 Claims, 2 Drawing Sheets

METHOD AND APPARATUS FOR INTERNAL FIXATION OF FRACTURES

BACKGROUND OF THE INVENTION

1. Field of the Invention

This invention relates to the fixation of bone fractures and more particularly, to the fixation of severely fractured bones where one or more bone pieces or fragments must be aligned with and secured to the major portion of the bone to promote healing. In a preferred embodiment the invention includes a method and apparatus for internal fixation of fractures, and severe fractures in particular, by utilizing non-metallic, preferably bioabsorbable fixation devices such as screws and pins, to temporarily align the bone fragments with the major portion of the bone and facilitate application of a reconstruction plate or like protective device. Mounting of the reconstruction plate or alternative fixation device on the major portion of the bone and the bone fragments is accomplished with conventional metal plates, screws, clamps and/or pins which may be applied without regard to the location of the non-metallic screws and pins.

Fractures of the human skeletal system have been treated by fixation with metal plates, screws and pins for many years. A problem which frequently arises with regard to this form of treatment is the technical difficulty encountered with fractures having multiple pieces or fragments. These fragments must be assembled and held in place in approximate anatomical alignment with some initial fixation until a plate or plates can be shaped to fit the contour of the bone and subsequently attached. In the past, this initial fixation has been accomplished by means of metal pins and screws, the placement and alignment of which is rendered difficult, particularly because the screw holes in the permanent metal reconstruction plate(s) frequently align with the metal screws and/or pins in the initial fixation effort. Accordingly, the holes cannot be properly drilled through these metal fixation devices without deviation of the drill bit, a problem which requires repositioning and recontouring of the reconstruction plate, with resulting compromise of final fixation, correct anatomical bone alignment and proper healing of the fracture.

The method and apparatus for internal fixation of fractures of this invention utilizes non-metallic, preferably bioabsorbable screws and pins which are inserted flush with the bone in the initial fixation process to faciliate attachment of a permanent metal reconstruction plate or plates in the most optimum position without concern for the position of the initial internal fixation devices. Pilot holes for the permanent metal screws which secure the metal reconstruction plate may then be drilled without regard to the position of the non-metallic fixation devices in place, since the latter are non-metallic and therefore soft and easily drilled or partially drilled without misaligning the pilot hole and companion metal screw or pin. Loss of fracture reduction which is accomplished in the initial fixation procedure is not likely to be lost under such circumstances, since clamps are normally placed about the bone and metal plate to stabilize the fracture and plate for final attachment. Furthermore, debris and cuttings from the non-metallic, bioabsorbable material poses no problem, since this material is resorbed by the body.

2. Description of the Prior Art

Various techniques and apparatus have been utilized in the past for achieving fixation of bone fractures. Typical of prior art patents covering such techniques is U.S. Pat. No. 2,242,003, dated May 13, 1941, to F. A. Lorenzo, entitled "Method and Apparatus for Reduction of Fracture of Femur". The method includes positioning the bone elements adjacent to the fracture in correct anatomical relationship, boring a hole through the upper shaft portion axially of the neck and terminating in the head portion, boring a second hole through the bone elements parallel to the first hole, inserting rigid pin members into the holes, which pins cooperate to prevent relative rotation of the head with respect to the neck, increasing the diameter of the hole axially of the neck while the pin is seated in the hole and inserting a canulated screw having deep threads formed with thin, sharp crests into the first hole telescopically with respect to the pin, to fix the head to the neck and afterwards, withdrawing the pins. U.S. Pat. No. 3,030,951, dated Apr. 24, 1962, to M. P. Mandarino, details "Methods and Materials For Orthopedic Surgery". The method includes introducing a partially polymerized, viscous liquid mixture and a polymerization catalyst into the space between bone segments to be united, allowing the liquid mixture to set and cementing the bone segments to each other. U.S. Pat. No. 3,579,831, dated May 25, 1971, to Irving J. Stevens, et al, details a "Bone Implant" such as a dental implant to be received in a jaw bone. The bone implant includes a screw which has a pair of opposed end regions, one of which is threaded for the purpose of screwing into bone and the other of which is provided with a mechanism for fastening any other desired structure to the screw. In addition to the screw, the bone implant includes at least one stabilizing pin operatively connected with the screw to stabilize the pin and the bone. U.S. Pat. No. 4,049,102, dated Nov. 22, 1977, to M. B. Devas, details "Bone Securing Devices". One of the devices includes a bone screw having leading and trailing end portions with respective threads of opposite hands. The leading end portion is more narrow than the trailing end portion and either/or both portions can be tapered toward their leading ends. U.S. Pat. No. 4,539,981, dated Sep. 10, 1985, to D. C. Tunc, details an "Absorbable Bone Fixation Device". The device is constructed from a high molecular weight polymer of L(−) lactide having an inherent viscosity above 4.5. The polymer contains less than 2% unreacted monomer and is polymerized under conditions of selected monomer-to-catalyst ratios and temperatures. A "Bio-Compatible Retention Pin And A Prosthesis Including Such A Pin" is detailed in U.S. Pat. No. 4,711,234, dated Dec. 8, 1987, to Michael Vives, et al. The retention pin is adapted to fix a support plate or other prosthesis on bone tissue. The pin is constructed of a material which is bio-compatible with human tissue and includes two-half pins, each having a half-head for bearing against the prosthesis and a retention shank projecting therefrom, with the outline of each shank being semi-cylindrical and the two half-pins being generated symmetrical to each other about a radial separation plane passing at least partially along the axis of the pin and extending at least as far as the inside faces of the half-heads from which the respective tension shanks project. The shanks are of sufficient length to project beyond a wall of bone by a distance which is not less than the diameter of the fixing hole, through the bone to enable locking means in the vicinity of the free end of the pin to urge the two half-pins apart from each other and resiliently over at least a portion of their length, against the inside wall of the fixing hole. U.S. Pat. No. 4,776,329, dated Oct. 11, 1988, to Richard Treharne, details a "Resorbable Compressing Screw and Method". The method includes a technique for repairing a bone fracture with a compression screw assembly. First and second non-resorbable compression members are positioned so that the head portion of the compression screw may protrude from the surface of the second non-resorbable compression member after further compression is effected by the normal healing process. At least the head portion of the screw is formed to a material that resorbs upon contact with body fluids. U.S. Pat. No. 4,858,603, dated Aug. 22, 1989, to A. J. T. Clemow, et al, details a "Bone Pin" constructed with a tapered polymeric portion and a cutting device secured to the smaller end of the polymeric portion. The pin can be inserted through a bone or bone fragment and the cutting device removed. U.S. Pat. No. 4,973,333, dated Nov. 27, 1990, to Richard Treharne, details a "Resorbable Compressing Screw and Method". The patent covers a compression hip screw for repairing a bone fracture which is characterized by a non-absorbable plate and a non-absorbable barrel section connected to the plate and adapted to be inserted into a hole formed in the hip bone. A non-absorbable lag screw with a longitudinal opening therein and having internal and external threads is adapted to be inserted through the longitudinal opening in the barrel and into the portion of the bone on one side of the fracture. A compressing screw with threads adapted to cooperate with the internal thread of the lag screw and a head adapted to abut the outer portion of the barrel adjacent to the longitudinal opening can be inserted into the opening in the barrel for compressing the portions of the bone on both sides of the fracture. The compressing screw has at least a head portion formed of a material that absorbs on contact with body fluids. An "Interference Fixation Screw With Integral Instrumentation" is detailed in U.S. Pat. No. 5,062,843, dated Nov. 5, 1991, to Thomas H. Mahoney, III. The fixation screw is designed for securing a bone graft of a tendon section and placed in the ligament tunnel and is formed from a bio-compatible plastic or bioabsorbable material. The tendon section is used to replace a ligament and has a tendon section attached at each end to bone grafts. The fixation screw is tightened between the bone graft and bones surrounding the ligament tunnel to secure the bone graft in place by forcing it against the bone surrounding the ligament tunnel.

It is an object of this invention to provide a method for more precise and stable fixation of fractures which promotes correct anatomical bone position and faster healing with less chance of bone fixation failure.

Another object of this invention is to provide a method and apparatus for internal fixation of bone fractures which reduces operation and tourniquet time and therefore reduces operative complications such as swelling and infection, as well as hospital and rehabilitation time.

Still another object of this invention is to provide a method and apparatus for internal fixation of bone fractures which includes using non-metallic fixtures for temporarily internally fixing bone fractures and facilitating application of one or more metal reconstruction plates by conventional metal screws and use of metal pins without regard to the location of the temporary non-metallic fixation members.

Yet another object of the invention is to provide a new use for bioabsorbable, non-metallic bone fixture devices such as screws and pins, in non-exclusive particular, to temporarily position fractured bones in at least approximately correct anatomical position and subsequently permanently securing the fracture by use of metal plates, screws and pins without regard for the location of the bioabsorbable, non-metallic bone fracture fixation devices.

SUMMARY OF THE INVENTION

These and other objects of the invention are provided in a method and apparatus for internal fixation of bone fractures, which method includes the steps of positioning the fractured bone elements in substantially correct anatomical relationship, drilling pilot holes through the bone fragments, inserting non-metallic, biocompatible and preferably, bioabsorbable, resorbable, non-metal fixation devices in the pilot holes to temporarily maintain the bone elements in proper anatomical alignment, then contouring a permanent metal reconstruction plate and attaching the plate by drilling appropriate additional pilot holes through openings in the plate into the bone elements without regard to the location of the biocompatible, resorbable, non-metal fixation devices and inserting metallic screws and/or pins through the holes in the reconstruction plate and the pilot holes into the bone to secure the reconstruction plate on the bone.

BRIEF DESCRIPTION OF THE DRAWINGS

The invention will be better understood by reference to the accompanying drawings, wherein.

DESCRIPTION OF THE PREFERRED EMBODIMENTS

Figure 1:
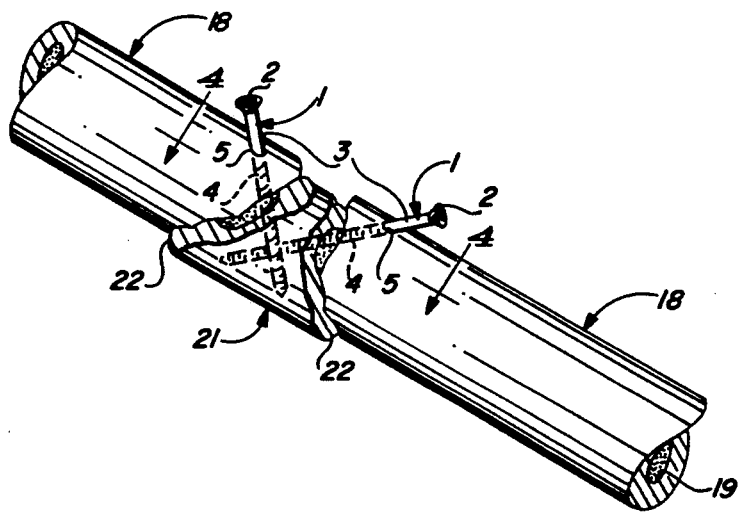
FIG. 1 is a perspective exploded view of a bone fracture and implementation of a preferred preliminary fracture reconstruction technique of this invention.

Referring initially to FIG. 1 of the drawings, a fractured bone 18 is illustrated, with a bone fragment 21 spaced from the two primary sections of the bone 18 at fracture lines 22. The bone marrow 19 of the bone 18 is also illustrated. The temporary fixation pilot holes 5 are angularly drilled in the two primary sections of the bone 18 and the bone fragment 21 and are designed to receive a pair of non-metallic, biocompatible, preferably bioabsorbable screws 1, in the crossed configuration illustrated in FIG. 1. The non-metallic screws 1 are each characterized by a non-metallic screw head 2, mounted on one end of a non-metallic screw shank 3, fitted with non-metallic screw threads 4, for engaging the temporary fixation pilot holes 5 and tightening the non-metallic screw threads 4 in the bone fragment 21. It will be appreciated from a consideration of FIG. 1 that the non-metallic screws 1 are characterized by a cortical screw design, that is, the shank porton of the bioabsorbable screw 1 is defined by a continuous non-metallic screw threads 4, according to the knowledge of those skilled in the art.

Figure 2:
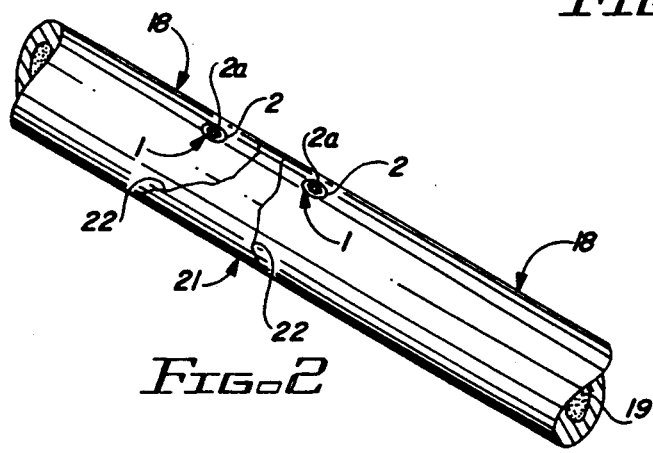
FIG. 2 is a perspective view of the bone and bone fragments temporarily secured in correct aligned anatomical position according to the fracture reconstruction technique illustrated in FIG. 1.

Referring now to FIG. 2 of the drawings, when the non-metallic screws 1 are tightened using a hex head screwdriver (not illustrated) for engaging the respective hex head slots 2a, the bone fragment 21 is drawn to the respective segments of the bone 18 in correct anatomical relationship along the fracture lines 22. Accordingly, the bone 18 and bone fragment 21 are aligned correctly, but temporarily, with the non-metallic screw heads 2 countersunk in the surface of the bone 18 according to well known techniques, to facilitate further treatment, as hereinafter further described.

Figure 3:
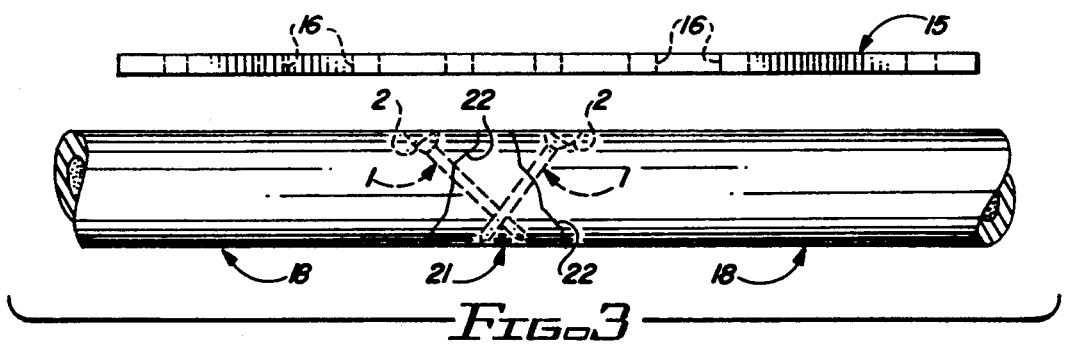
FIG. 3 is a side view of the correctly aligned bone and bone fragments illustrated in FIG. 2, with a metal reconstruction plate spaced from the bone above the fracture.
Figure 4:
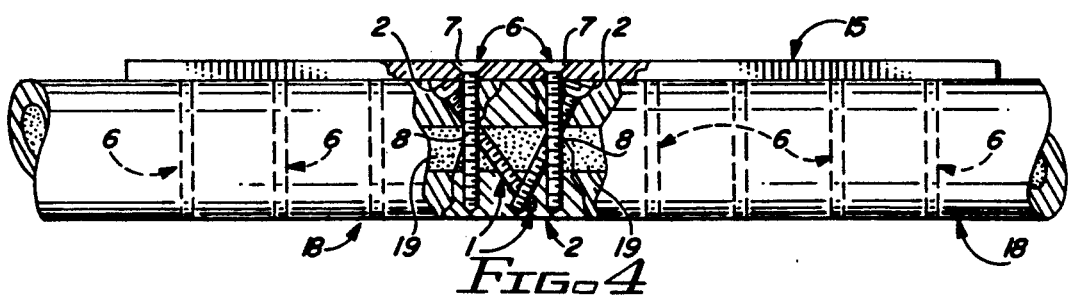
FIG. 4 is a side view, partially in section, of the metal reconstruction plate mounted to the bone and bone fragment according to the fracture reconstruction technique illustrated in FIGS. 1-3.

Referring now to FIGS. 3 and 4 of the drawings, after the bone 18 and bone fragment 21 are temporarily correctly anatomically aligned by means of the non-metallic screws 1 as illustrated in FIG. 2, a conventional metal reconstruction plate 15, having spaced screw access openings 16, is shaped to fit the bone 18 over the bone fragment 21 and fracture lines 22. The metal reconstruction plate 15 is placed on the outside surface of the bone 18 and the bone fragment 21 as illustrated in FIG. 4, and additional pilot holes are drilled into the bone 18 and the bone fragment 21 in transverse relationship at the respective screw access openings 16. Conventional metal cortical screws 6, having hex screw heads 7 and cortical screw threads 8, are then inserted in the screw openings 16 and threadably extended into the pilot holes in the bone 18 and the bone fragment 21 as illustrated in FIG. 4, without regard to the location of the non-metallic screws 1. In this manner, the reconstruction plate 15 is tightly secured to the bone 18 and the bone fragment 21 by means of the metal cortical screws 6, and the bone 18 and bone fragment 21 are permanently maintained in correct anatomical alignment.

Figure 7:
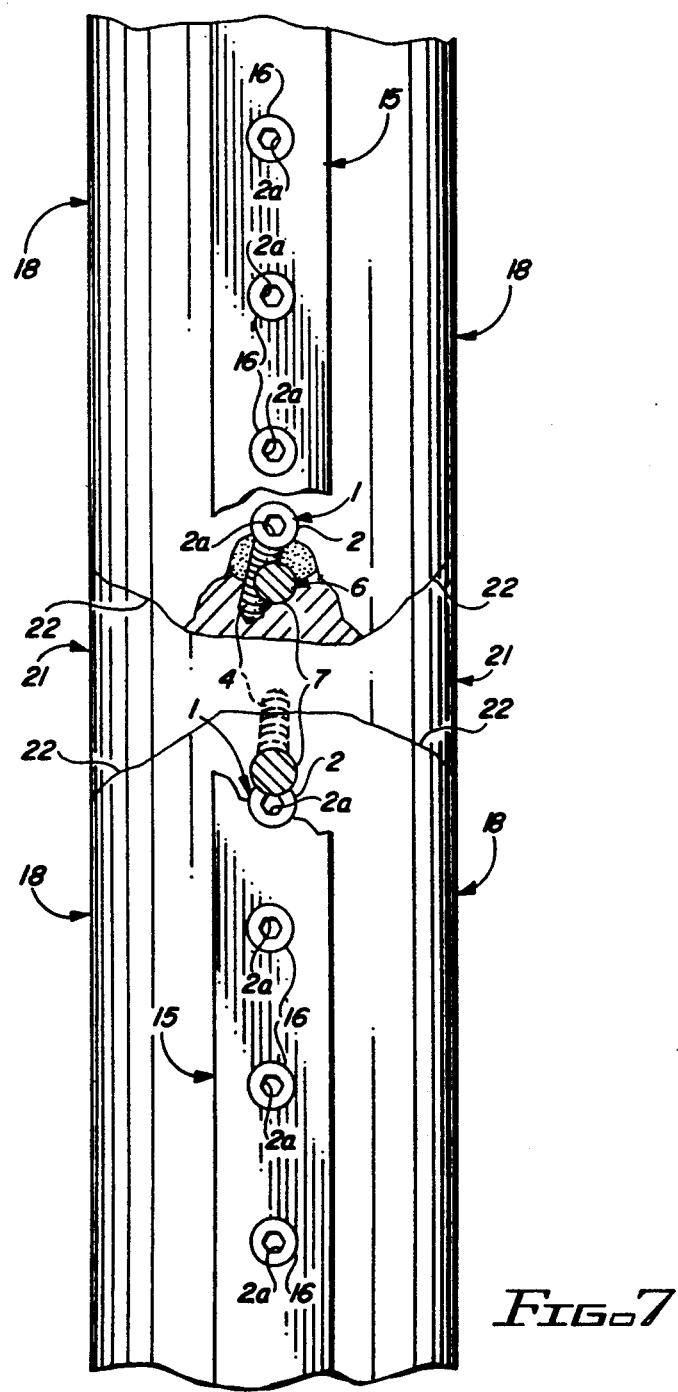
FIG. 7 is an enlarged top view, partially in section, of a metal reconstruction plate mounted on the bone and bone fragment, more particularly illustrating the location of a pair of metal cortical screws intersecting corresponding partially drilled non-metallic, biocompatible and preferably, bioabsorbable screws according to the technique of this invention.

Referring now to FIG. 7 of the drawings, it will be appreciated by those skilled in the art that accurate and precise application of the metal reconstruction plate 15 to the bone 18 and bone fragment 21 depends upon the non-metallic, relatively soft nature of the temporary non-metallic screws 1. Accordingly, the permanent fixation pilot holes may be drilled through the bone 18 and the bone fragment 21 in transverse or alternative relationship with respect to the bone 18 without regard to the location of the previously inserted non-metallic screws 1, since these pilot holes may pass directly through all or a portion of the relatively soft non-metallic screws 1, without deviation of the drill bit and compromising alignment of the reconstruction plate 15. Subsequently, the metal cortical screws 6 may be threaded into these drilled pilot openings in the bone 18 and bone fragment 21, through the drilled segments of the non-metallic screws 1 without misaligning or otherwise compromising the position of the metal reconstruction plate 15. With time, the bioabsorbable non-metallic screws 1 are resorbed into the body, while the metal cortical screws 6 remain in position to secure the metal reconstruction plate 15 tightly on the bone 18 and the bone fragment 21, which normally heals along the fracture lines 22, to maintain the bone 18 and bone fragment 21 in correct anatomical alignment. However, it is understood that non-resorbable, non-biocompatible non-metallic fixation devices may be used in orthopedic surgical procedures where the bioabsorbable character of the fixation devices is not a factor in the promotion of healing or the longevity of the reconstruction.

Figure 5:
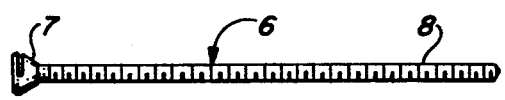
FIG. 5 is a side view of a typical cortical screw used in orthopedic surgery.
Figure 6:
FIG. 6 is a side view of a typical cancellous screw used in orthopedic surgery.

Referring now to FIGS. 5 and 6 of the drawings, FIG. 5 illustrates a conventional cortical screw 6, having a cortical screw head 7 and cortical screw threads 8 extending along the entire shank portion of the cortical screw 6. Similarly, FIG. 6 illustrates a cancellous screw 10, which includes a cancellous screw head 11 and a smooth cancellous screw shank 12 projecting from the cancellous screw head 11 and fitted with cancellous screw threads 13 along the lower portion thereof. It will be appreciated by those skilled in the art that the cortical screw 6 illustrated in FIG. 5 and the cancellous screw 10 illustrated in FIG. 6 are conventional metal screws normally constructed of stainless steel, which have long been used for orthopedic purposes in the fixation of fractures. Both the cortical screw head 7 and the cancellous screw head 11 are provided with a head hex slot or alternative recess (not illustrated) for driving purposes. It will be further appreciated by those skilled in the art that the non-metallic screw 1 illustrated in FIGS. 1–4 and 7 of the drawings may also be constructed of a bioabsorbable or bioresorbable material fashioned in the configuration of the cortical screw 6 illustrated in FIG. 5 and the cancellous screw 10 illustrated in FIG. 6. For example, various configurations of the non-metallic screw 1 may be constructed of the absorbable bone fixation material detailed in U.S. Pat. No. 4,539,981, dated Sep. 10, 1985, to D. C. Tunc. That patent details an "Absorbable Internal Bone Fixation Device" constructed from a high molecular weight polymer of L(—) lactide having an inherent viscosity above 4.5. These devices are said to be absorbable in the human body and need not be removed after the bone is healed. Other such materials which may be suitable for fabrication of the non-metallic screw 1, as well as alternative bioabsorbable fixation devices, are synthetic absorbable polymers detailed in U.S. Pat. Nos. 3,463,158; 3,636,956; 3,739,773; 3,797,499; and 3,839,297. These bone fixation devices are constructed from synthetic polymers which are either polylactides, polyglycolides or copolymers of lactide and glycolide. The device detailed in U.S. Pat. No. 4,539,981 is stated to be formable into such fixation devices as plates, screws, wires, rods, pins, staples, cable ties and clips.

It will be further appreciated by those skilled in the art that the non-metallic screw 1 illustrated in FIGS. 1–4 and 7 of the drawings need not necessarily be constructed of a bioabsorbable or bioresorbable material, but may also be constructed of a plastic or alternative material which is characterized by sufficient load-bearing strength for the temporary internal bone fixation procedures of this invention. However, as noted above, in a most preferred embodiment of the invention, these non-metallic screws are bioabsorbable or bioresorbable for ultimate removal by the body and more complete healing. Moreover, whether constructed of bioabsorbable or bioresorbable material or not, the non-metallic fixation devices envisioned by this invention may be shaped to define screws, pins and other surgically important devices, according to the knowledge of those skilled in the art.

It will be further appreciated by those skilled in the art that the non-metallic screws 1 and other temporary fixation devices may selectively be bioabsorbable or biocompatible and when used according to the techniques of this invention, may be applied by conventional tools which are used to apply metallic counterparts of the fixation devices. Accordingly, conventional drills, screwdrivers, clamps and like devices, in non-exclusive particular, can all be utilized by the orthopedic surgeon to apply and remove, as necessary, the various internal fixation devices of this invention without additional expense and confusion associated with multiple pieces of equipment.

While the preferred embodiments of the invention have been described above, it will be recognized and understood that various modifications may be made therein and the appended claims are intended to cover all such modifications which may fall within the spirit and scope of the invention.

Having described my invention with the particularity set forth above, what is claimed is:

1. A method for internal fixation of bone fractures comprising the steps of positioning bone elements of the fractures in correct anatomical relationship; drilling at least one temporary fixation hole in the bone elements across the fractures; inserting at least one non-metallic fixation device in said temporary fixation hole for temporarily securing the bone elements in the correct anatomical relationship; fitting at least one metal permanent reconstruction means to the bone elements; drilling at least two permanent fixation holes in the bone elements without regard to the location of said non-metallic fixation device; and inserting metallic fixation devices in said permanent fixation holes for securing said reconstruction means on said bone elements and said bone elements in the correct anatomical relationship.

2. The method according to claim 1 wherein said non-metallic fixation device further comprises a bioabsorbable non-metallic fixation device.

3. The method according to claim 1 wherein said non-metallic fixation device further comprises a cortical screw.

4. The method according to claim 3 wherein said cortical screw is constructed of a bioabsorbable material.

5. The method according to claim 1 wherein said non-metallic fixation device further comprises a cancellous screw.

6. The method according to claim 5 wherein said cancellous screw is constructed of a bioabsorbable material.

7. The method according to claim 1 wherein said metallic fixation devices further comprise metal screws.

8. The method according to claim 7 wherein said non-metallic fixation device further comprises a bioabsorbable non-metallic fixation device.

9. A method for internal fixation of bone fractures comprising the steps of positioning bone elements of the fractures in substantially correct anatomical relationship; drilling temporary fixation pilot holes in the bone elements across the fractures; inserting non-metallic, bioabsorbable fixation devices in said temporary fixation holes, respectively, for temporarily securing the bone elements in the substantially correct anatomical relationship; fitting at least one permanent metal reconstruction means to the bone elements; drilling a plurality of permanent fixation holes in the bone elements without regard to the location of said non-metallic bioabsorbable fixation devices; and inserting metallic fixation devices in said permanent fixation holes for securing said reconstruction means on said bone elements and said bone elements in the correct anatomical relationship.

10. The method according to claim 9 wherein said non-metallic, bioabsorbable fixation devices are cortical screws.

11. The method according to claim 9 wherein said non-metallic, bioabsorbable fixation devices are cancellous screws.

* * * * *